US010405762B2

(12) United States Patent
Teixeira

(10) Patent No.: US 10,405,762 B2
(45) Date of Patent: Sep. 10, 2019

(54) SYSTEM AND METHOD FOR NONINVASIVELY MEASURING VENTRICULAR STROKE VOLUME AND CARDIAC OUTPUT

(71) Applicant: Streamline Automation LLC, Huntsville, AL (US)

(72) Inventor: Rodrigo E. Teixeira, Madison, AL (US)

(73) Assignee: Vital Metrix, Inc., Huntsville, AL (US)

( * ) Notice: Subject to any disclaimer, the term of this patent is extended or adjusted under 35 U.S.C. 154(b) by 372 days.

(21) Appl. No.: 15/225,803

(22) Filed: Aug. 1, 2016

(65) Prior Publication Data
US 2017/0119261 A1 May 4, 2017

Related U.S. Application Data

(63) Continuation-in-part of application No. 12/640,278, filed on Dec. 17, 2009, now abandoned.

(60) Provisional application No. 61/171,802, filed on Apr. 22, 2009.

(51) Int. Cl.
*A61B 5/0205* (2006.01)
*A61B 5/1455* (2006.01)
*A61B 5/00* (2006.01)
*A61B 5/024* (2006.01)
*A61B 5/021* (2006.01)
*A61B 5/08* (2006.01)
*G06F 17/18* (2006.01)
*A61B 5/0295* (2006.01)
*G06K 9/00* (2006.01)
*G06K 9/62* (2006.01)

(52) U.S. Cl.
CPC .......... *A61B 5/0295* (2013.01); *A61B 5/0205* (2013.01); *A61B 5/14551* (2013.01); *A61B 5/6826* (2013.01); *G06K 9/00523* (2013.01); *G06K 9/6226* (2013.01); *A61B 5/021* (2013.01); *A61B 5/02416* (2013.01); *A61B 5/0816* (2013.01); *A61B 5/7203* (2013.01); *A61B 5/7267* (2013.01); *A61B 5/7405* (2013.01); *A61B 5/7455* (2013.01)

(58) Field of Classification Search
None
See application file for complete search history.

(56) References Cited

U.S. PATENT DOCUMENTS 5,626,140 A * 5/1997 Feldman .............. G06K 9/6293
600/483

OTHER PUBLICATIONS

Awad et al. (J. Clinical Monitoring and Computing, 2006, 20, 175-184.*
Tax et al. Pattern Recognition, 2000, 33, 1475-1485.*

* cited by examiner

*Primary Examiner* — Michael L Borin
(74) *Attorney, Agent, or Firm* — Patent Grove LLC; Thomas Friend

(57) ABSTRACT

A system for non-invasively measuring cardiac output, stroke volume, or both comprises a pulse oximeter, a data processor, and means for generating an output reporting measured one or more CO or SV values to a user. A method for non-invasively measuring cardiac output, stroke volume, or both comprises collecting plethysmographic waveform data of a patient, providing the plethysmographic waveform to a data processor, and calculating measured values for CO or SV. The data processor comprises a mathematical model of the cardiovascular system integrated in a dynamic state space model (DSSM).

12 Claims, 14 Drawing Sheets

SYSTEM AND METHOD FOR NONINVASIVELY MEASURING VENTRICULAR STROKE VOLUME AND CARDIAC OUTPUT

CROSS-REFERENCE TO RELATED APPLICATIONS

This application is a continuation-in-part of U.S. Ser. No. 12/640,278 filed Dec. 17, 2009, which is non-provisional of U.S. 61/171,802 filed Apr. 22, 2009. This application is additionally related to the following US patent applications: Ser. No. 12/796,512 filed Jun. 8, 2010, issued as U.S. Pat. No. 9,060,722;
Ser. No. 13/096,845 filed Apr. 28, 2011, issued as U.S. Pat. No. 9,173,574;
Ser. No. 13/096,876 filed Apr. 28, 2011, issued as U.S. Pat. No. 9,275,171;
Ser. No. 13/096,904 filed Apr. 28, 2011; Ser. No.
Ser. No. 13/181,027 filed Jul. 12, 2011, issued as U.S. Pat. No. 8,494,829;
Ser. No. 13/181,140 filed Jul. 12, 2011; and Ser. No.
Ser. No. 13/181,247 filed Jul. 12, 2011.

STATEMENT REGARDING FEDERALLY SPONSORED RESEARCH OR DEVELOPMENT

The U.S. Government may have certain rights to this invention pursuant to Contract Number IIP-0839734 awarded by the National Science Foundation.

BACKGROUND OF THE INVENTION

Field of the Invention

The present invention relates generally to apparatus, systems, and methods for noninvasively measuring cardiac output (CO) and left ventricular stroke volume (SV). More specifically, the invention includes systems and methods that measure CO and/or SV using plethysmographic waveform data collected by a pulse oximeter.

Description of Related Art

There has been a long felt need in the medical arts for a noninvasive way to measure left ventricular stroke volume (SV) and cardiac output (CO). SV is the volume of blood pumped by the left ventricle of the heart with a single heart cycle. CO is the product of SV and hear rate (HR). SV and CO are important physiological parameters for a number of medical conditions, including congestive heart failure (CHF).

Patients being treated for heart failure are normally medicated with drugs that regulate diuresis and heart muscle function. An important aim of drug therapy is to maintain a CO that is sufficient to perfuse tissues with oxygenated blood. It is advantageous to use the lowest possible doses of drugs to manage CHF because the drugs used produce unwanted side effects. To optimally manage the dosage and selection of drugs in the treatment of CHF, one must monitor CO to assess the efficacy of the drugs and dosages being administered and/or to monitor patient compliance.

Currently, CO is measured using invasive techniques such as the Fick method, the Thermodilution method, and implantable microelectromechanical devices (MEMs), also called CardioMEMs. The Fick method involves the measurement of oxygen consumption and computing the arteriovenous difference using samples of arterial blood and mixed venous blood from the pulmonary artery. The thermodilution method measures the rate at which cold saline solution is diluted in the blood. Both of these methods are performed in a hospital setting because they require the placement of a catheter in the pulmonary artery. Additionally, the use of a pulmonary artery catheter use may also increase morbidity in critically ill patients. CardioMEMs are surgically implanted into patients in a hospital setting and, once implanted, provide measurements of SV and CO that can be used to monitor patients. The implantation of the cardioMEMs device into the pulmonary artery, however, is expensive and is performed in a hospital setting and involves the risks associated with heart catheterization.

Less invasive techniques for measuring SV and CO include esophageal Doppler and transesophageal echocardiography. Esophageal Doppler measures blood flow velocity in the descending thoracic aorta using a flexible ultrasound probe that is inserted into the esophagus. The blood flow velocity is combined with an estimate of the cross-sectional area of the aorta estimated from the patient's age, height, and weight to calculate SV and CO. This technique requires someone with technical skill to insert an esophageal Doppler monitor, which must be properly aligned with respect to the thoracic aorta to provide accurate measurements. Transesophageal echocardiography involves measuring SV using flow velocity calculated from the area under the measured Doppler velocity waveform at the pulmonary artery, the mitral valve, or the aortic valve. This technique requires a highly trained operator to position and place the esophageal Doppler monitor. These procedures are not truly noninvasive because accessing the esophagus is perceived by patients as invasively uncomfortable.

Truly noninvasive methods, apparatus, and systems are needed that can measure SV and CO, preferably in the homes of patients without the need for skilled caregivers. Pulse oximetry has been investigated for decades as a possible tool for the noninvasive measurement of SV and CO. A pulse oximeter (PO) is a device that obtains photoplethysmography (PPG) data, which measures changes in blood volume within a tissue caused by the pulse of blood pressure through the vasculature in the tissue. The blood volume change is detected by measuring the amount of light transmitted or reflected to a sensor from a light source used to illuminate the skin. The shape of the PPG waveform varies with the location and manner in which the pulse oximeter is contacted with the body. In addition to PPG data, a pulse oximeter measures peripheral oxygen saturation (SpO2). Most often, the device operates in a transmission mode in which two wavelengths of light are passed through a body part to a photodetector. Changes in absorbance at each of the wavelengths are measured, which allow the determination of the absorbance due to pulsing arterial blood, excluding venous blood, skin, bone, muscle, and other tissues. Alternatively, reflectance pulse oximetry can be used. A typical pulse oximeter comprises a data processor and a pair of light-emitting diodes (LEDs) facing a photodiode. One LED produces red light having a wavelength of 660 nm, the other infrared light having a wavelength of 940 nm. Oxygenated hemoglobin absorbs more infrared light and less red light than hemoglobin. The transmission signals fluctuate over time because of changes in the amount of arterial blood present in the tissue caused by the blood pulse associated with each cycle of the heart. The ratio of red light measured to infrared light measured is calculated by the processor and is converted by the processor to SpO2 using a lookup table based on the Beer-Lambert law.

Awad et al. (J. Clinical Monitoring and Computing, 2006, 20:175-184) reports that researchers have been attempting to understand the relationship between central cardiac hemodynamics and the resulting measured peripheral waveforms. Awad et al. studied ear pulse oximeter waveforms in order to understand the underlying physiology reflected in these waveforms and to extract information about cardiac performance. Multi-linear regression analysis of ear plethysmographic waveform components were used to estimate CO from the ear plethysmograph and it was determined that ear plethysmographic width correlates with CO. Awad et al. does not suggest that this correlation allows pulse oximetry or plethysmographic data to be used to calculate SV or CO.

Natalini et al. (Anesth. Analg. 2006, 103:1478-1484) reports the use of pulse oximetry to predict which hypotensive patients are likely to respond positively to increasing blood volume. Arterial blood pressure changes during mechanical ventilation are reported as accurately predicting fluid responsiveness. Photoplethysmographic (PPG) waveform variations measured by pulse oximetry showed a correlation with measured pulse pressure variation values associated with fluid responsiveness but neither SV nor CO were calculated. Natilini does not indicate that SV or CO can be calculated using PPG data.

US 2013/0310669 discloses a method for determining mixed venous oxygen saturation (SvO2) using a photoplethysmography pulse oximeter (PPG PO) device that measures changes in pulmonary circulation using a light source and a light detector applied to the thoracic wall of a patient. The light source and the detector are separated by at least 15-20 mm so that the region of illumination overlaps a portion of the pulmonary microcirculation beneath the PPG device. The contribution of circulation in the thoracic wall to the PPG signal must be assessed using an additional detector and/or light source that is attached to the thoracic wall less than 8 mm apart. The SvO2 value can be used to calculate CO using the Fick method from the values of total oxygen consumption, arterial oxygen content and venous oxygen content. One drawback of this method is that the pulmonary microcirculation is surrounded by bone, muscle, and other tissues that make the contribution of circulation in the thoracic wall to the PPG signal difficult to measure reliably. Another drawback is that the measured values depend on the accurate placement of the light emitters and sensors, which may be difficult to reproduce for each subsequent measurement.

U.S. Pat. No. 9,289,133 discloses a method and apparatus for monitoring proportional changes in CO from a blood pressure signal measurement obtained by fingertip PPG. A time constant of the arterial tree is defined as the product of the total peripheral resistance (TPR) and a constant arterial compliance and is determined by analyzing long time scale variations of more than one cardiac cycle. A value proportional to CO is determined from the ratio of the blood pressure signal to the estimated time constant using Ohm's law. An invasive, absolute CO calibrating measurement is required to derive absolute CO values from the proportional CO change values obtained using PPG. This method and apparatus cannot measure values for SV or CO without an invasive CO measurement and therefore requires a hospital setting and skilled medical personnel.

WO 2010/0274102 A1 discloses a data processing method and associated apparatus and systems that measures SV and CO from pulse oximetry data. The pulse oximeter system comprises a data processor configured to perform a method that combines a probabilistic processor and a physiological model of the cardiovascular system in a Dynamic State-Space Model (DSSM) that can remove contaminating noise and artifacts from the pulse oximeter sensor output and measure blood oxygen saturation, HR, SV, aortic pressure and systemic pressures. This pulse oximeter and associated method provides truly noninvasive measurement of CO and SV suitable for monitoring patients with CHF. The DSSM comprises a mathematical model of the cardiovascular system that models the physiological processes which produce the pulses measured by the pulse oximeter. In one embodiment, the model comprises parameters including aortic pressure, radial pressure, peripheral resistance, aortic impedance, and blood density.

BRIEF SUMMARY OF THE INVENTION

The present invention fills a need in the art for truly noninvasive apparatus and methods for measuring SV and CO by providing a system and method for measuring and reporting SV and/or CO using plethysmographic (PG) waveform data from a photoplethysomgraphic pulse oximeter (PPG PO).

DETAILED DESCRIPTION OF THE INVENTION

As used herein, "noninvasively" and "noninvasive" are used to indicate that a method, system, or apparatus does not involve an invasive or minimally invasive procedure such as surgery or catheterization. Additionally, "noninvasively" and "noninvasive" are used to indicate that a method, system, or apparatus does not involve endoscopy, phlebotomy, biopsy, or a procedure that requires intubation or artificial respiration.

Figure 1:
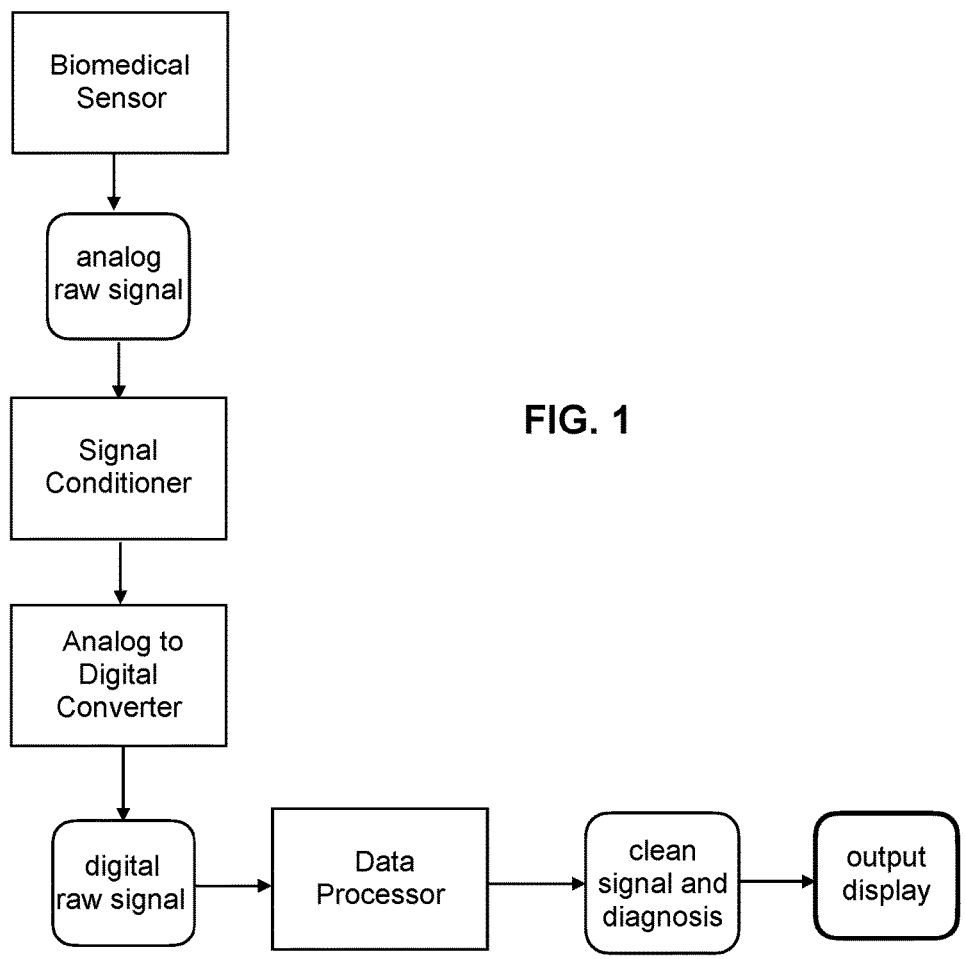
FIG. 1 is a flow chart showing the path of information flow from a biomedical sensor to a data processor and on to an output display according to one embodiment of the invention.

FIG. 1 is a top-level schematic for data processing according to the present invention. A biomedical sensor, such as pulse oximeter, normally produces a raw analog output signal that is converted to a raw digital output signal. The analog to digital conversion may also be accompanied by signal filtering or conditioning. Digital signals are received by a data processor configured to process the digital data and produce a processed (or clean) signal comprising an estimated true value for the physiological parameter being measured. The processed signal is then displayed, for example, in the form of an electronic, hard copy, audible, visual, and/or tactile output. The output may be used, for example, by a user to monitor a patient, by a user for self monitoring, or by a user as biofeedback process.

The data processor shown in FIG. 1 is configured to receive, as input data, digital signals from one or more biomedical sensors, and enter the data into a dynamic state-space model (DSSM) integrated with a processor engine. The integrated DSSM/processor engine produces transformed output data that may correspond to a physiological parameter measured by the biomedical sensor(s), in the form of an estimated true value for the physiological parameter. The processor engine may operate in a dual estimation mode (a dual estimation engine) or in a joint estimation mode (a join estimation engine). The output may include additional outputs corresponding to physiological parameters not measured by the physiological sensor(s), diagnostic information, and a confidence interval representing the probability that the output estimated value(s) for the physiological parameter(s) is accurate. The data transformation process performed by the data processor may be used to remove artifacts from the input data to produce output data having higher accuracy than the input data and/or to extract information from the input data to generate output data estimating the values for physiological parameters that are not otherwise measured or reported using data from the sensor(s). In the case of a pulse oximeter, the physiological parameter(s) that are not otherwise measured may include SV, and/or CO.

Mathematical and Computational Models

A mathematical model or a computer model, as used herein, involves the use of state parameters and model parameters in a mathematical representation of physiological processes that give rise to a physiological parameter being measured and processes through which sensor data is detected.

A mathematical model may include model and/or state parameters that correspond directly to physiological parameters including vital signs such as oxygen saturation of blood ($SpO_2$), heart rate (HR), respiratory rate (RR), and blood pressure (BP) that can be directly measured; physiological parameters not directly measured such as total blood volume (TBV), left-ventricular stroke volume (SV), vasomotor tone (VT), autonomous nervous system (ANS) tone, and cardiac output (CO); and hemoglobin-bound complexes, concentrations of metabolic intermediates, and concentrations of drugs present in one or more tissues or organs.

While the scope of a mathematical model used in the context of the present invention cannot possibly encompass every single process of human physiology, it should have the capacity to interpret the measured observable(s). For instance, if the intent is to process electrocardiography (ECG) signals, a model describing the generation and propagation of electrical impulses in the heart should be included.

The fusion of two or more biomedical signals follows the same principle. For instance, if the intent is to measure blood pressure waves and electrocardiogram signals simultaneously, the use of a heart model describing both the electrical and mechanical aspects of the organ should be used. Initially, the model may also accept manual data input as a complement to data from sensors. Nonlimiting examples of manually entered data include food consumption over time vital signs, gender, age, weight, and height.

Non-physiological models may be included in and/or coupled to the DSSM in cases where non-biomedical signals are measured. For instance, one may use non-biomedical measurements to enhance or complement biomedical measurements. A non-limiting example is the use of accelerometer data to enhance motion artifact rejection in biomedical measurements. In order to accomplish this, the physiological model is extended to describe both measurements, which may include, in this example, cardiovascular circulation at rest, at different body postures (standing, supine, etc), and in motion.

Dynamic State-Space Model

Figure 2:
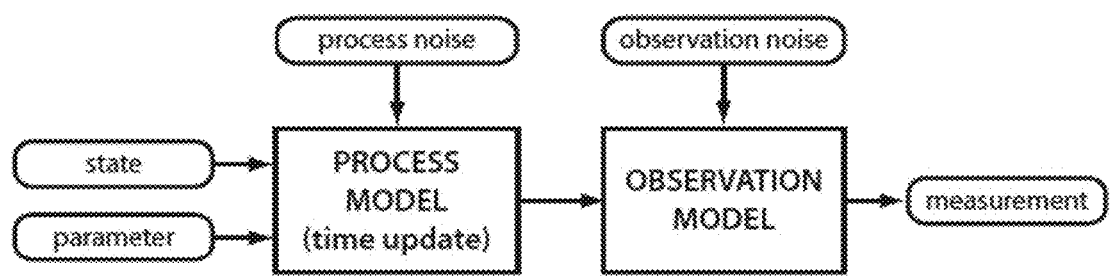
FIG. 2 is a flow chart showing inputs, outputs, and conceptual division of model parts for a dynamic state-space model (DSSM).
Figure 3:
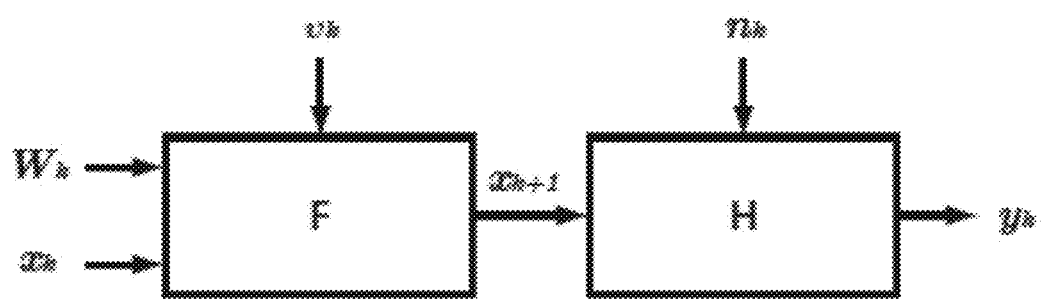
FIG. 3 is a block diagram showing mathematical representations of inputs, output and conceptual divisions of the DSSM shown in FIG. 2.

FIG. 2 and FIG. 3 show schematics of one embodiment of a dynamic state-space model (DSSM) used in the processing of data according to the present invention. The DSSM comprises a process model F that mathematically represents physiological processes involved in generating one or more physiological parameters measured by a biomedical sensor and describes the state of the subject over time in terms of state parameters. This mathematical model optimally includes mathematical representations accounting for process noise such as physiologically caused artifacts that may cause the sensor to produce a digital output that does not produce an accurate measurement for the physiological parameter being sensed. The DSSM also comprises an observational model H that mathematically represents processes involved in collecting sensor data measured by the biomedical sensor. This mathematical model optimally includes mathematical representations accounting for observation noise produced by the sensor apparatus that may cause the sensor to produce a digital output that does not produce an accurate measurement for a physiological parameter being sensed. Noise terms in the mathematical models are not required to be additive.

While the process and observational mathematical models F and H may be conceptualized as separate models, they are normally integrated into a single mathematical model that describes processes that produce a physiological parameter and processes involved in sensing the physiological parameter. That model, in turn, is integrated with a processing engine within an executable program stored in a data processor that is configured to receive digital data from one or more sensors and to output data to a display or other output formats.

FIG. 3 provides mathematical descriptions of the inputs and outputs corresponding to FIG. 2. Initially, values for state parameters, preferably in the form of a state vector $x_k$, are received by the DSSM together with input model parameters $W_k$. Process noise $v_k$ and observation noise $n_k$ are also received by the DSSM, which updates the state parameter vector and model parameter vector and produces an output observation vector $y_k$. Once the model is initialized, the updated state vector $x_{k+1}$, updated model parameters $W_{k+1}$, and time-specific sensor data are used as input for each calculation for subsequent iterations, or time steps.

The DSSM is integrated in a dual estimation processing engine or a joint estimation processing engine. The most favored embodiment makes use of a DSSM built into a Sigma point Kalman filter (SPKF) or Sequential Monte Carlo (SMC) processing engine. Sigma point Kalman filter (SPKF), as used herein, refers to the collective name used for derivativeless Kalman filters that employ the deterministic sampling based sigma point approach to calculate approximations of the optimal terms of the Gaussian approximate linear Bayesian update rule, including unscented, central difference, square-root unscented, and square-root central difference Kalman filters. SMC and SPKF processing engines operate on a general nonlinear DSSM having the form:

$$x_k = f(x_{k-1}, v_{k-1}; W) \quad (1)$$

$$y_k = h(x_k, n_k; W) \quad (2)$$

A hidden system state, $x_k$, propagates over time index, k, according to the system model, f. The process noise is $v_{k-1}$, and W is the vector of model parameters. Observations, $y_k$, about the hidden state are given by the observation model h and $n_k$ is the measurement noise. When W is fixed, only state estimation is required and either SMC or SPKF can be used to estimate the hidden states.

Unsupervised Machine Learning

Unsupervised machine learning, sometimes referred to as system identification or parameter estimation, involves determining the nonlinear mapping:

$$y_k = g(x_k; w_k) \quad (3)$$

where xk is the input, yk is the output, and the nonlinear map g(.) is parameterized by the model parameter vector W. The nonlinear map, for example, may be a feed-forward neural network, recurrent neural network, expectation maximization algorithm, or enhanced Kalman filter algorithm. Learning corresponds to estimating W in some optimal fashion. In the preferred embodiment, SPKF or SMC is used for updating parameter estimates. One way to accomplish this is to write a new state-space representation $$W_{k+1} = w_k + r_k \quad (4)$$

$$d_k = g(x_k; w_k) + e_k \quad (5)$$

where $w_k$ correspond to a stationary process with identity state transition matrix, driven by process noise $r_k$. The desired output $d_k$ corresponds to a nonlinear observation on $w_k$.

Dual Estimation Engine for Estimation of State and Model Parameters

Figure 4:
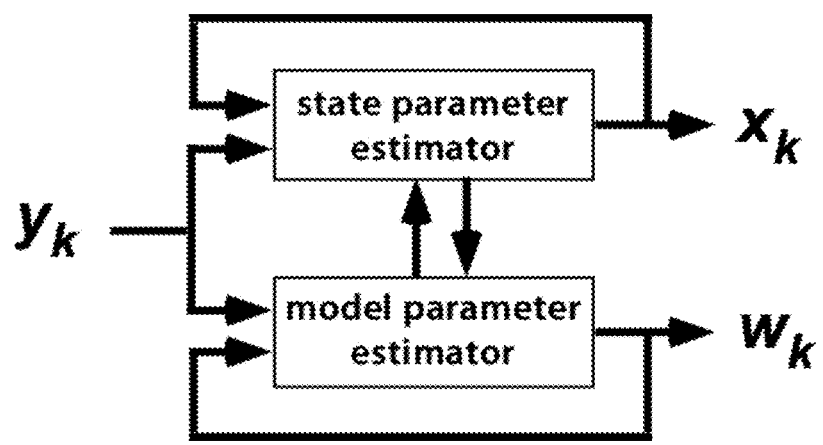
FIG. 4 is a mathematical representation of the process of dual estimation.
Figure 5:
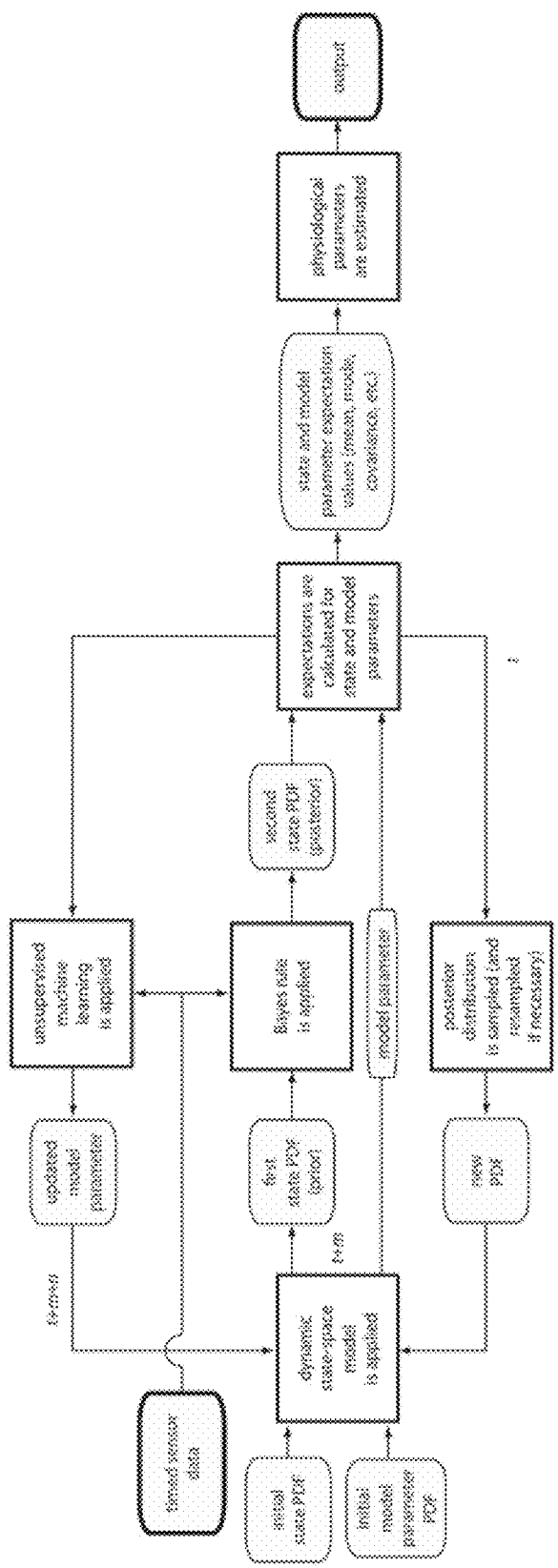
FIG. 5 is a schematic diagram showing the process steps involved in a dual estimation process.

The state and parameter estimation steps may be coupled in an iterative dual-estimation mode as shown in FIGS. 4 and 5. This formulation for a state estimator operates on an adaptive DSSM. In the dual estimation process, states $x_k$ and parameters W are estimated sequentially inside a loop. When used in a data processor for a pulse oximeter, the current state $x_k$ from pulse oximeter sensor input $y_k$. States $x_k$, and parameters W are estimated sequentially inside a loop. Parameter estimates are passed from the previous iteration to state estimation for the current iteration. Several different implementations or variants of the SMC and SPKF methods exist, including the sigma-point, Gaussian-sum, and square-root forms. The particular choice may be influenced by the application.

The current estimate of the parameters $W_k$ is used in the state estimator as a given (known) input, and likewise the current estimate of the state $x_k$ is used in the parameter estimator. This results in a step-wise stochastic optimization within the combined state-parameter space.

The flow chart shown FIG. 5 provides a summary of the steps involved in dual estimation process. Initial probability distributions for state and model parameters are provided to the DSSM to produce an initial probability distribution function (first PDF or prior PDF) representing the initial state. Data for a time $t_1$ from a sensor (new measurement) and the initial PDF are combined using a Bayesian statistical process to generate a second, posterior PDF that represents the state at the time of the measurement for the first sensor data. Expectation values for the second PDF are calculated, which may represent the most likely true value. Expectation values may also represent, for instance, the confidence interval or any statistical measure of uncertainty associated with the value. Based upon the expectation values, usually but not necessarily the values for state parameters having the highest probability of being correct, updated state parameters for time $t_1$ are combined with sensor data for time $t_1$ to update the model parameters for time $t_2$ in the DSSM by the process shown in FIG. 4. The expectation values are also fed into the DSSM as the state, in the form of a vector of state parameters (new PDF) as shown in FIG. 4. Once the state parameters and model parameters for the DSSM are updated to time $t_1$, the process is repeated with timed data for time $t_2$ to produce updated parameters for time $t_2$ and so forth. The time interval between time steps is usually constant such that time points may be described as t, t+n, t+2n, etc. If the time interval is not constant, then the time may be described using two or more time intervals as t, t+n, t+n+m, etc.

Joint Estimation Engine for Estimation of State and Model Parameters

Figure 6:
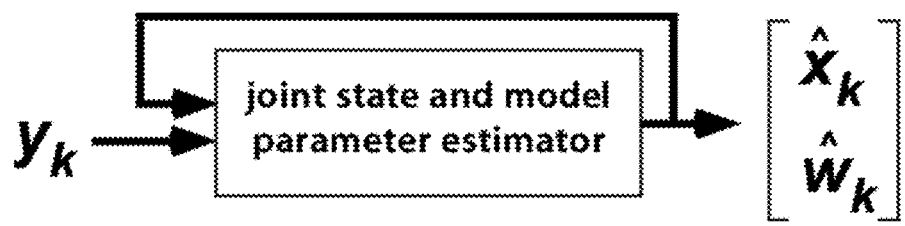
FIG. 6 is a mathematical representation of the process of joint estimation.
Figure 7:
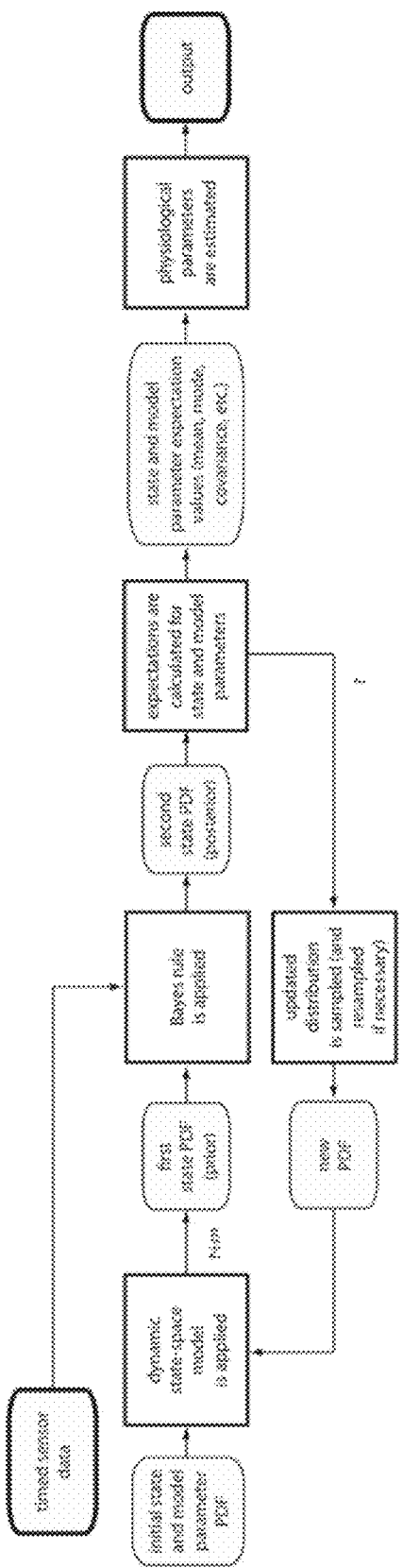
FIG. 7 is a schematic diagram showing the process steps involved in a joint estimation process.

The state and parameter estimation steps may also be performed in a simultaneous joint-estimation mode as shown in FIGS. 6 and 7. The calculated variables for the state parameters and model parameters of the physiological model are concatenated into a single higher-dimensional joint state vector:

$$X = [x_k^T \ w_k^T]^T \quad (6)$$

where $x_k$ are the state parameters and $w_k$ the model parameters. The joint state space is used to produce simultaneous estimates of the states and parameters.

The flow chart shown FIG. 7 provides a summary of the steps involved in dual estimation process. The process is similar to that shown for dual estimation in FIG. 5, with the exception that model and state parameters are not separated into two separate vectors, but are represented together in a single vector. The process is initiated by entering a vector representing initial state and model parameter value distributions into the DSSM and producing an initial first PDF. The first PDF is combined with sensor data (new measurement) for time $t_1$ in a Bayesian statistical process to generate a second, posterior PDF that represents the state and model parameters at time $t_1$. Expectation values for the second PDF are calculated, which may represent the most likely true value. Expectation values may also represent, for instance, the confidence interval or any statistical measure of uncertainty associated with the value. Based upon the expectation values, updated state and model parameters for time $t_1$ are entered into the DSSM by the process shown in FIG. 6. Once the state parameters and model parameters for the DSSM are updated to time $t_1$, the process is repeated with timed data for time $t_2$ to produce updated parameters for time $t_2$ and so forth.

Compared to dual estimation, both state and model parameters are concatenated into a single vector that is transformed by the DSSM. Hence, no machine learning step is necessary in order to update model parameters. Joint estimation may be performed using a sequential Monte Carlo method or sigma-point Kalman method. These may take the form of unscented, central difference, square-root unscented, and square-root central difference forms. The optimal method will depend on the particular application.

Sequential Monte Carlo Methods

SMC methods estimate the probability distributions of all the model unknowns by propagating a large number of samples called probability particles in accordance with the system models (typically nonlinear, non-Gaussian, non-stationary) and the rules of probability. Artifacts are equivalent to noise with short-lived probability distributions, also called non-stationary distributions. The number of simulated particles scales linearly with computational power, with 100 particles being reasonable for real time processing with presently available processors. The system model describes pertinent physiology and the processor engine uses the system model as a "template" from which to calculate, using Bayesian statistics, posterior probability distribution functions (processed data). From this, the expectation values (e.g. the mean) and confidence intervals can be estimated FIG. 7. The combination of SMC with Bayesian Statistics to calculate posterior probability distribution functions is often referred to as a Particle Filter.

SMC process nonlinear and non-Gaussian problems by discretizing the posterior into weighted samples, or probability particles, and evolving them using Monte Carlo simulation. For discretization, Monte Carlo simulation uses weighted particles to map integrals to discrete sums:

$$p(x_k \mid y_{1:k}) \approx \hat{p}(x_k \mid y_{1:k}) = \sum_{i=1}^{n} \delta(x_k - x_k^{(i)}) \tag{7}$$

where the random samples $\{x(i); i=1, 2, \ldots, N\}$, are drawn from $p(x_k \mid y_{1:k})$ and $\delta(.)$ is the Dirac delta function. Expectations of the form $$E[g(x_h)] = \int g(x_h) p(x_h \mid y_{1:k}) dx_h \tag{8}$$

can be approximated by the estimate:

$$E[g(x_k)] \approx \tilde{E}[g(x_k)] = \frac{1}{N} \sum_{i=1}^{N} g(x_k^{(i)}) \tag{9}$$

if the distribution has finite support. As N approaches infinity, the estimate converges to the true expectation.

The optimal Bayesian solution can be outlined by the following recursive algorithm. Suppose the required PDF a $p(x_{k-1} \mid y_{t:k-1})$ at time k−1 is available. In the prediction stage, the prior PDF at time k is obtained using the DSSM via the Chapman-Kolmogorov equation:

$$p(x_k \mid y_{1:k-1}) = \int p(x_h \mid x_{k-1}) p(x_{k-1} \mid y_{1:k-1}) dx_{k-1} \tag{10}$$

The DSSM model describing the state evolution $p(x_k \mid x_{k-1})$ is defined by the system equation (1) and the known statistics of $v_{k-1}$. At time step k a measurement $y_k$ becomes available, and this may be used to update the prior (updated stage) via Bayes' rule:

$$p(x_k \mid y_{1:k}) = \frac{p(y_k \mid x_k) p(x_k \mid y_{1:k-1})}{p(y_k \mid y_{1:k-1})} \tag{11}$$

where the normalizing constant $$p(y_k \mid y_{1:k-1}) = \int p(y_k \mid x_k) p(x_k \mid y_{1:k-1}) dx_k \tag{12}$$

depends on the likelihood function $p(y_k \mid x_k)$ defined by the measurement model (equation 2) and the known statistics of $n_k$.

It is not possible to sample directly from the posterior density function so importance sampling from a known proposal distribution $\pi(x_{0:k} \mid y_{1:k})$ is used. One may use sigma-point Kalman filters, for example, to generate the proposal.

The known distribution is introduced into Equation 5 to yield:

$$E[g(x_{0:k})] = \int g(x_{0:k}) \frac{w_k(x_{0:k})}{p(y_{1:k})} \pi(x_{0:k} \mid y_{1:k}) dx_{0:k} \tag{13}$$

where the variables $w_k(x_{0:k})$ are unnormalized importance weights, which are written as $w_k(x_{0:k}) = w_k$:

$$w_k(x_{0:k}) = \frac{p(y_{1:k} \mid x_{0:k}) p(x_{0:k})}{\pi(x_{0:k} \mid y_{1:k})} \tag{14}$$

resulting in a weighted expectation:

$$E[g(x_{0:k})] \approx \tilde{E}[g(x_{0:k})] = \sum_{i=1}^{N} \tilde{w}_k^{(i)} g(x_{0:k}^{(i)}) \tag{15}$$

where $\tilde{w}_h^{(i)}$ are normalized importance weights:

$$\tilde{w}_k^{(i)} = w_k^{(i)} \bigg/ \sum_{j=1}^{N} w_k^{(j)} \tag{16}$$

Importance sampling is made sequential by reiterating the Markov $1^{st}$ order assumption, resulting in the assumption that the current state is not dependent on future observations:

$$\pi(x_{0:k} \mid y_{1:h}) = \pi(x_{0:h-1} \mid y_{1:k-1}) \pi(x_h \mid x_{0:h-1}, y_{1:h}) \tag{17}$$

and that observations are conditionally independent given the states:

$$p(x_{0:k}) = p(x_0) \prod_{j=1}^{k} p(x_j \mid x_{j-1}) \tag{18}$$

$$p(y_{1:k} \mid x_{0:k}) = \prod_{j=1}^{k} p(y_j \mid x_j) \tag{19}$$

A recursive estimate for the importance weights is:

$$w_k = w_{k-1} \frac{p(y_k \mid x_k) p(x_k \mid x_{k-1})}{\pi(x_k \mid x_{0:k-1}, y_{1:k})} \tag{20}$$

which is called Sequential Importance Sampling (SIS). SIS suffers from degeneracy so that, over a few iterations, all but one of the importance weights will be zero, effectively removing a large number of samples. To remedy this, samples with low importance weights may be eliminated while high importance samples may be multiplied. One way to accomplish this is Sampling-Importance Resampling (SIR), which involves mapping the Dirac random measure $$\{x_h^{(i)}, \tilde{w}_h^{(i)}; i=1, \ldots N\} \quad (21)$$

into a measure with equal weights, $1/N$:

$$\left\{x_k^{(j)}, \frac{1}{N}; i=1, \ldots, N\right\} \quad (22)$$

A pseudo-code for a generic SMC (also called bootstrap filter or condensation algorithm) can be written as:
1. Importance sampling step. For $i=1, \ldots, N$, do:

$$x_h^{(i)} \sim p(x_h | x_{k-1}^{(i)}) \quad \text{i) sample}$$

$$w_h^{(i)} \sim w_{h-1}^{(i)} p(y_h | x_h^{(i)}) \quad \text{ii) evaluate}$$

$$\tilde{w}_k^{(i)} = w_h^{(i)} / \Sigma_{j=1}^N w_h^{(i)} \quad \text{iii) normalize}$$

2. Importance resampling step
   i) eliminate or multiply samples $x_h^{(i)}$ according to weights $\tilde{w}_h^{(i)}$ to obtain N random samples approximately distributed according to $p(x_h | y_{1:h})$
   ii) For $i=1, \ldots N$, set $w_h^{(i)} = \tilde{w}_h^{(i)} = N^{-1}$
3. Output
   i) any expectation, for instance:

$$\hat{x}_k = E[x_k | y_{1:k}] \approx \frac{1}{N} \sum_{i=1}^N x_h^{(i)}$$

SPKF may be used to approximate probability distributions. Assuming that x has a mean $\bar{x}$ covariance $P_x$, and dimension L, a set of $2L+1$ weighted sigma-points, $S_i = \{w_i, X_i\}$, is chosen according to:

$$X_0 = \bar{x} \quad (23)$$

$$X_i = \bar{x} + \left(h\sqrt{P_x}\right)_i \quad i=1, \ldots, L$$

$$X_i = \bar{x} - \left(h\sqrt{P_x}\right)_i \quad i=L+1, \ldots, 2L$$

$$w_0^{(m)} = \frac{h^2 - L}{h^2}$$

$$w_i^{(m)} = \frac{1}{2h^2} \quad i=1, \ldots, 2L$$

$$w_i^{(o1)} = \frac{1}{4h^2} \quad i=1, \ldots, 2L$$

$$w_i^{(o1)} = \frac{h^2 - 1}{4h^4} \quad i=1, \ldots, 2L$$

where h is a scaling parameter. Each sigma-point is propagated through the DSSM to yield the posterior sigma-point set, $Y_i$:

$$Y_i = h(f(X_i)), i=0, \ldots 2L \quad (24)$$

From this, the posterior statistics are calculated using a procedure resembling the linear Kalman filter. For instance, for the unscented Kalman filter case, a SPKF variant, the time-update equations are:

$$X_{k|k-1}^x = f(X_{k-1}^x, X_{k-1}^x, u_{k-1}) \quad (25)$$

$$\hat{x}_k^- = \sum_{i=0}^{2L} w_i^{(m)} X_{i,k|k-1}^x \quad (26)$$

$$P_{x_k}^- = \sum_{i=0}^{2L} w_i^{(o)} (X_{i,k|k-1}^x - \hat{x}_k^-)(X_{i,k|k-1}^x - \hat{x}_k^-)^T \quad (27)$$

and the measurement-update equations are:

$$Y_{k|k-1} = h(X_{k|k-1}^x - X_{k-1}^x) \quad (28)$$

$$\hat{y}_k^- = \sum_{i=n}^{2L} w_i^{(m)} Y_{i,k|k-1} \quad (29)$$

$$P_{\tilde{y}_k} = \sum_{i=0}^{2L} w_i^{(o)} (Y_{i,k|k-1} - \hat{y}_k^-)(Y_{i,k|k-1} - \hat{y}_k^-)^T \quad (30)$$

$$P_{x_k y_k} = \sum_{i=0}^{2L} w_i^{(o)} (X_{i,k|k-1}^x - \hat{x}_k^-)(Y_{i,k|k-1} - \hat{y}_k^-)^T \quad (31)$$

$$K_k = P_{x_k y_k} P_{\tilde{y}_k}^{-1} \quad (32)$$

$$\hat{x}_k = \hat{x}_k^- + K_k (y_k - \hat{y}_k^-) \quad (33)$$

$$P_{x_k} = P_{x_k}^- - K_k P_{\tilde{y}_k} K_k^T \quad (34)$$

where x, v and n superscripts denote the state, process noise and measurement noise dimensions, respectively.

The mathematical structure for sequential Monte Carlo and SPKF represent two examples of a family of probabilistic inference methods exploiting Monte Carlo simulation and the sigma point transform, respectively, in conjunction with a Bayesian statistical process.

SPKF are generally inferior to SMC but are computationally cheaper. Like SMC, SPKF evolve the state using the full nonlinear DSSM, but represent probability distributions using a sigma-point set. This is a deterministic step that replaces the stochastic Monte Carlo step in the SMC. As a result, SPKF lose accuracy when posterior distributions depart heavily from the Gaussian form, such as with bimodal or heavily-tailed distributions, or with strong nonstationary distributions such as those caused by motion artifacts in pulse oximeters. For these cases SMC are more suitable.

SPKF yields higher-order accuracy than the extended Kalman filter (EKF) and its related variants with equal algorithm complexity, $O(L^2)$. SPKF returns $2^{nd}$ order accuracy for nonlinear and non-Gaussian problems, and 3rd order for Gaussian problems. EKF has only $1^{st}$ order accuracy for nonlinear problems. Both EKF and SPKF approximate state distributions with Gaussian random variables (GRV). However, the EKF propagates the GRV using a single measure (usually the mean) and the $1^{st}$ order Taylor expansion of the nonlinear system. The SPKF, on the other hand, decomposes the GRV into distribution moments (sigma points) and propagates those using the unmodified nonlinear system. SPKF implementation is simpler than EKF since it is derivativeless. That is, it uses the unmodified DSSM form, and therefore does not require lengthy Jacobian derivations.

The data processing method is also capable of prediction because the method can operate faster than real time measurements. At any given time during data processing, the measurement PDF, obtained either from SPKF or SMC, embodies all available statistical information up to that point in time. It is therefore possible to march the system model forwards in time, for instance, using the same sequential Monte Carlo method, to obtain deterministic or stochastic simulations of future signal trajectories. In this way, the future health status (physiological state) of a patient can be predicted with attached probabilities indicating the confidence of each prediction.

Noise Adaptation

The data processing method may benefit from a noise adaptation method if timed sensor data contains noise and/or artifact that changes its spectral qualities over time. That is, if timed sensor data has a non-stationary probability distribution function. Here, a known algorithm such as the Robins-Monro or Annealing methods may be added to the data processing method in order to adapt the probability distribution functions of noise terms (stochastic terms) in the DSSM according to changing noise and artifact present in sensor data.

Output

In general, the output may include estimates of the true measured signals (i.e. processed data), and estimates of values for one or more physiological parameters measured by one or more sensors from which data was received, and estimates of values for one or more physiological parameters not measured by the sensors from which data was received (data extraction). A state parameter estimate is the processed data from the physiological sensor. Both noise and artifacts can be attenuated or rejected even though they may have very distinct probability distribution functions and may mimic the real signal. A model parameter estimate may be also used to produce a physiological parameter. For example, an estimate of total blood volume may be used to diagnose hemorrhage or hypovolemia. An estimate of tissue oxygen saturation may indicate poor tissue perfusion and/or hypoxia. Estimates of glucose uptake in several tissues may differentiate between diabetes mellitus types and severities; and estimates of carotid artery radius may be indicative of carotid artery stenosis.

EXAMPLES

Pulse Oximeter with Probabilistic Data Processing

Figure 8:
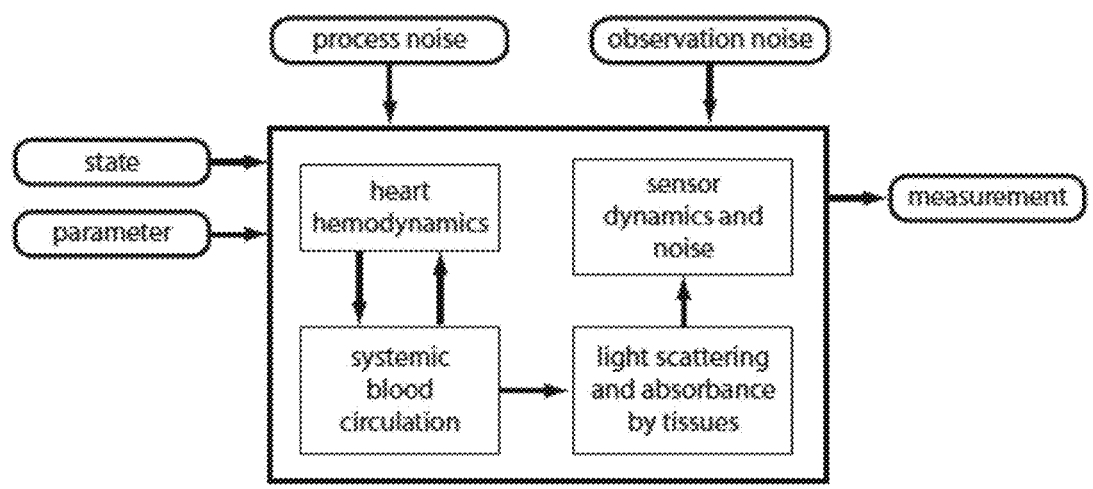
FIG. 8 is a flow chart showing the components of a DSSM used for pulse oximetry data processing.
Figure 9:
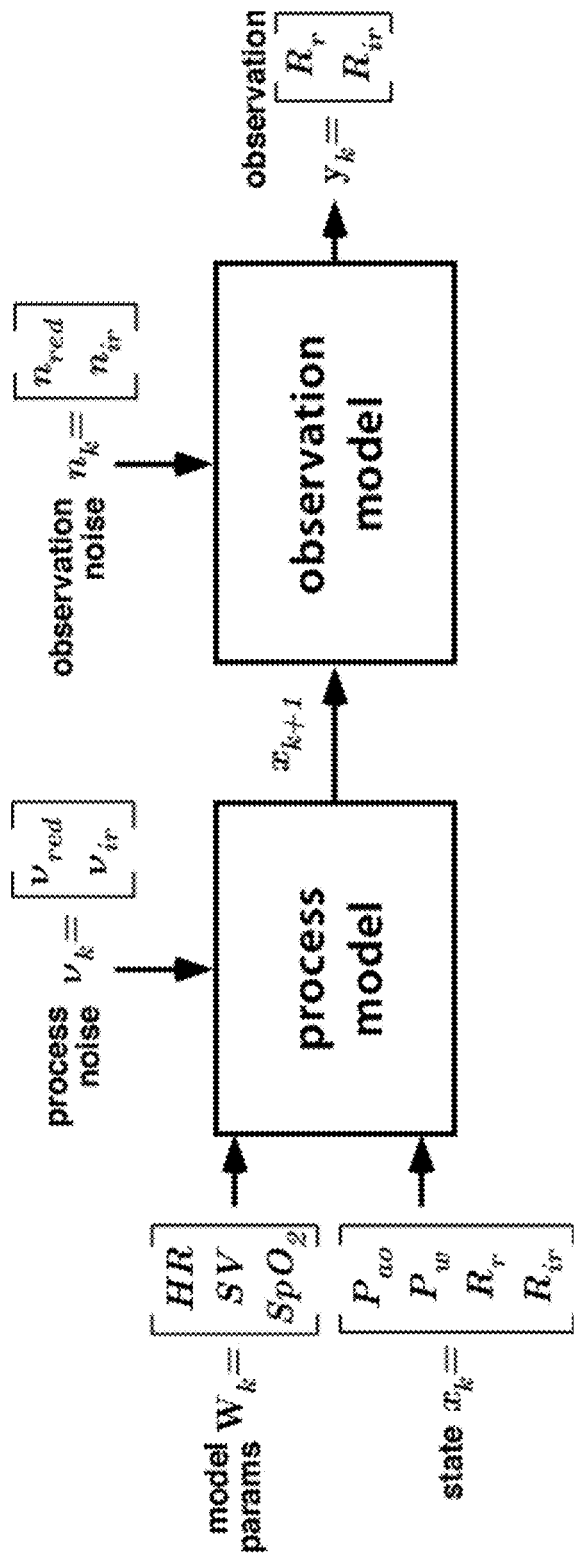
FIG. 9 is a flow chart showing examples of parameter inputs and outputs for a DSSM used for pulse oximetry data processing.

FIG. 8 shows the components of a DSSM suitable for processing data from a pulse oximeter, including components required to describe processes occurring in a subject. FIG. 9 illustrates the DSSM broken down into process and observation models, and including input and output variables. Heart rate (HR), stroke volume (SV) and whole-blood oxygen saturation ($SpO_2$) are estimated from input noisy red and infrared intensity ratios (R). Radial (Pw) and aortic (Pao) pressures are also available as state estimates.

In this example, the DSSM comprises the following function to represent CO:

$$Q_{CO}(t) = \overline{Q}_{CO} \sum_{k=1}^{5} a_k \exp\left[\frac{-(t-b_k)^2}{c_k^2}\right] \quad (31)$$

wherein CO Qco(t), is expressed as a function of HR and SV and where $Q_{CO}=(HR \times SV)/60$. The CO function pumps blood into a Windkessel 3-element model of the vascular system including two state parameters: aortic pressure, Pao, and radial (Windkessel) pressure, $P_W$:

$$P_{w,k+1} = \frac{1}{C_w R_p}((R_p + Z_o)Q_{CO} - P_{co,k}) \cdot \delta t + P_{w,k} \quad (32)$$

$$P_{co,k+1} = P_{w,k+1} + Z_o Q_{CO} \quad (33)$$

$R_P$ and $Z_O$ are the peripheral resistance and characteristic aortic impedance, respectively. The sum of these two terms is the total peripheral resistance due to viscous (Poiseuille-like) dissipation:

$$Z_o = \sqrt{\rho/AC_1} \quad (34)$$

where ρ is blood density. The elastic component due to vessel compliance is a nonlinear function including thoracic aortic cross-sectional area, A:

$$A(P_{co}) = A_{max}\left[\frac{1}{2} + \frac{1}{\pi}\arctan\left(\frac{P_{co}-P_0}{P_1}\right)\right] \quad (35)$$

where Amax, $P_0$ and $P_1$ are fitting constants correlated with age and gender:

$$A_{max}=(5.62-1.5(\text{gender})) \cdot \text{cm}^2 \quad (36)$$

$$P_0=(76-4(\text{gender})-0.89(\text{age})) \cdot \text{mmHg} \quad (37)$$

$$P_1=(57-0.044(\text{age})) \cdot \text{mmHg} \quad (38)$$

The time-varying Windkessel compliance, Cw, and the aortic compliance per unit length, Cl, are:

$$C_w = lC_l = l\frac{dA}{dP_{co}} = l\frac{A_{max}/(\pi P_1)}{1+\left(\frac{P_{co}-P_0}{P_1}\right)^2} \quad (39)$$

where l is the aortic effective length. The peripheral resistance is defined as the ratio of average pressure to average flow. A set-point pressure, Pset, and the instantaneous flow:

$$R_P = \frac{P_{set}}{(HR \cdot SV)/60} \quad (40)$$

are used to provide compensation autonomic nervous system responses. The value for Pset is adjusted manually to obtain 120 over 75 mmHg for a healthy individual at rest.

The compliance of blood vessels changes the interactions between light and tissues with pulse. This is accounted for using a homogenous photon diffusion theory for a reflectance or transmittance pulse oximeter configuration. For the reflectance case:

$$R = \frac{I_{ac}}{I_{dc}} = \frac{\Delta I}{I} = \frac{3}{2}\Sigma'_a K(\alpha, d, r)\sum_a^{art} \Delta V_a \quad (41)$$

for each wavelength. In this example, the red and infrared bands are centered at ~660 nm and ~880 nm. l denotes the detected intensities: total reflected (no subscript), and the pulsating (ac) and background (dc) components. Va is the arterial blood volume, which changes as the cross-sectional area of illuminated blood vessels, $\Delta A_w$, changes as:

$$\Delta V_a \approx r \cdot \Delta A_w \quad (42)$$

where r is the source-detector distance. The tissue scattering coefficient, $\Sigma s'$, is assumed constant but the arterial absorption coefficient, $\Sigma a^{art}$, depends on blood oxygen saturation, $SpO_2$:

$$\Sigma_a^{art} = \frac{H}{v_i}[SpO_2 \cdot \sigma_a^{100\%} + (1-SpO_2) \cdot \sigma_a^{0\%}] \quad (43)$$

which is the Beer-Lambert absorption coefficient, with hematocrit, H, and red blood cell volume, $v_i$. The optical absorption cross sections for red blood cells containing totally oxygenated ($HbO_2$) and totally deoxygenated (Hb) hemoglobin are $\sigma_a^{100\%}$ and $\sigma_a^{0\%}$, respectively.

The function $K(\alpha,d,r)$ contains, along with the scattering coefficient, the wavelength, sensor geometry and oxygen saturation dependencies that alter the effective optical path lengths:

$$K(\alpha, d, r) \approx \frac{-r^2}{1+\alpha r} \quad (44)$$

The attenuation coefficient $\alpha$ is:

$$\alpha \times 3\Sigma_a(\Sigma_s + \Sigma_a) \quad (45)$$

where $\Sigma_a$ and $\Sigma_s$ are whole-tissue absorption and scattering coefficients, respectively, which are calculated from Mie Theory.

Red and infrared K values as a function of $SpO_2$ may be represented by two linear fits:

$$\overline{K}_r \approx -4.03 \cdot SpO_2 - 1.17 \quad (46)$$

$$\overline{K}_{ir} \approx 0.102 \cdot SpO_2 - 0.753 \quad (47)$$

in $mm^2$. The overbar denotes the linear fit of the original function. The pulsatile behavior of $\Delta Aw$, which couples optical detection with the cardiovascular system model, is:

$$\Delta A_w = \frac{A_{w,max}}{\pi} \frac{P_{w,1}}{P_{w,1}^2 + (P_{w,k+1} - P_{w,0})^2} \Delta P_w \quad (48)$$

with $P_{w,0}=(\frac{1}{3})P_0$ and $P_{w,1}=(\frac{1}{3})P_1$ to account for the poorer compliance of arterioles and capillaries relative to the thoracic aorta. Third and fourth state variables, the red and infrared reflected intensity ratios, R=lac/ldc, are:

$$R_{r,k+1} = c\Sigma'_{s,r}\overline{K}_r\Sigma_{a,r}^{art}\Delta A_w + R_{r,k} + v_r \quad (49)$$

$$R_{ir,k+1} = c\Sigma'_{s,ir}\overline{K}_{ir}\Sigma_{a,ir}^{art}\Delta A_w + R_{ir,k} + v_{ir} \quad (50)$$

Here, v are Gaussian-distributed process noises intended to capture the baseline wander of the two channels. The constant c subsumes all factors common to both wavelengths and is treated as a calibration constant. The observation model adds Gaussian-distributed noises, n, to $R_r$ and $R_{ir}$:

$$\begin{bmatrix} y_{r,k} \\ y_{ir,k} \end{bmatrix} = \begin{bmatrix} R_{r,k} \\ R_{ir,k} \end{bmatrix} + \begin{bmatrix} n_{r,k} \\ n_{ir,k} \end{bmatrix} \quad (51)$$

Figure 11:
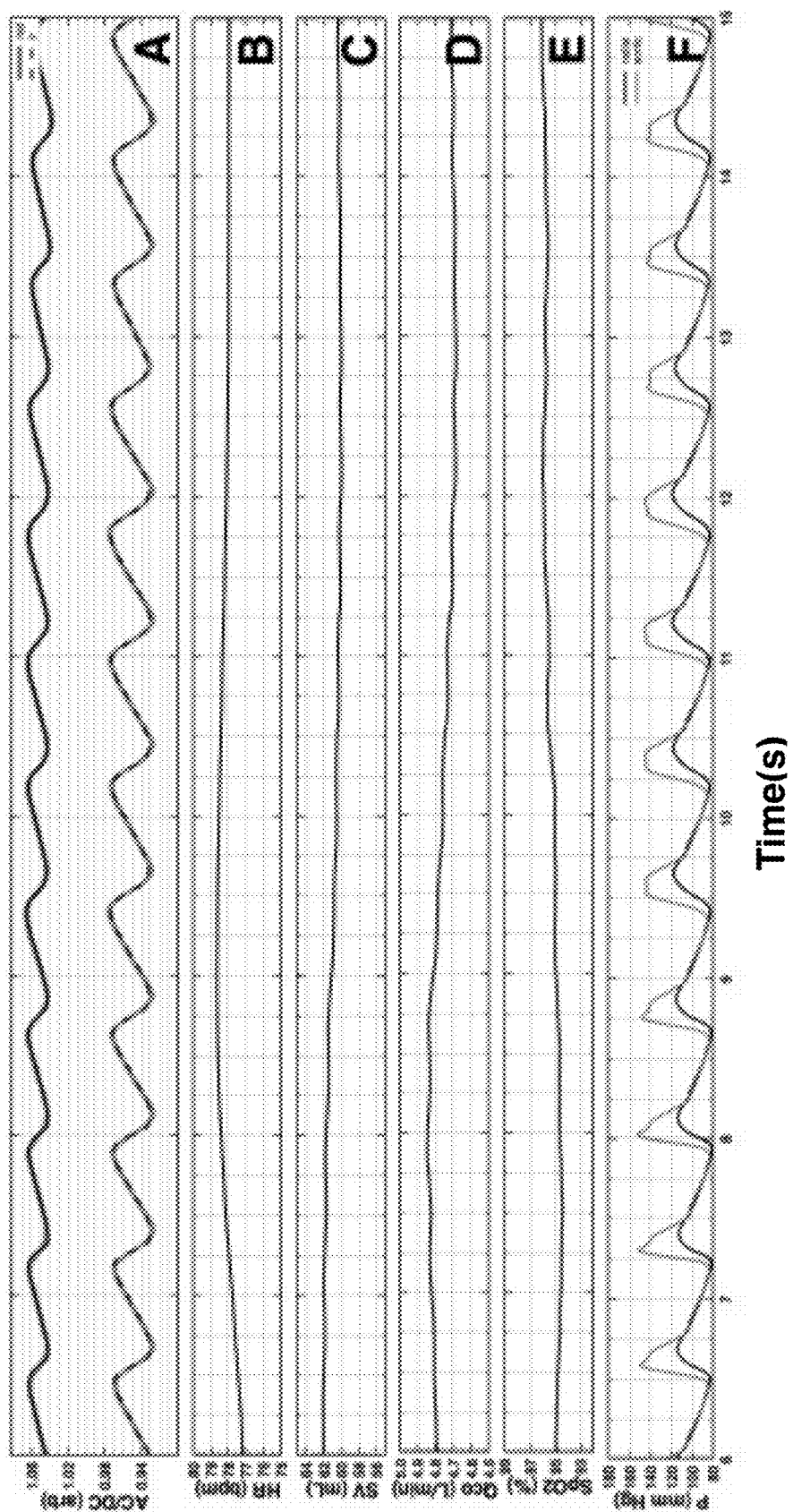
FIG. 11 is a chart showing input sensor data from a fingertip pulse oximeter and processed output data from a data processor configured to process pulse oximetry data.
Figure 12:
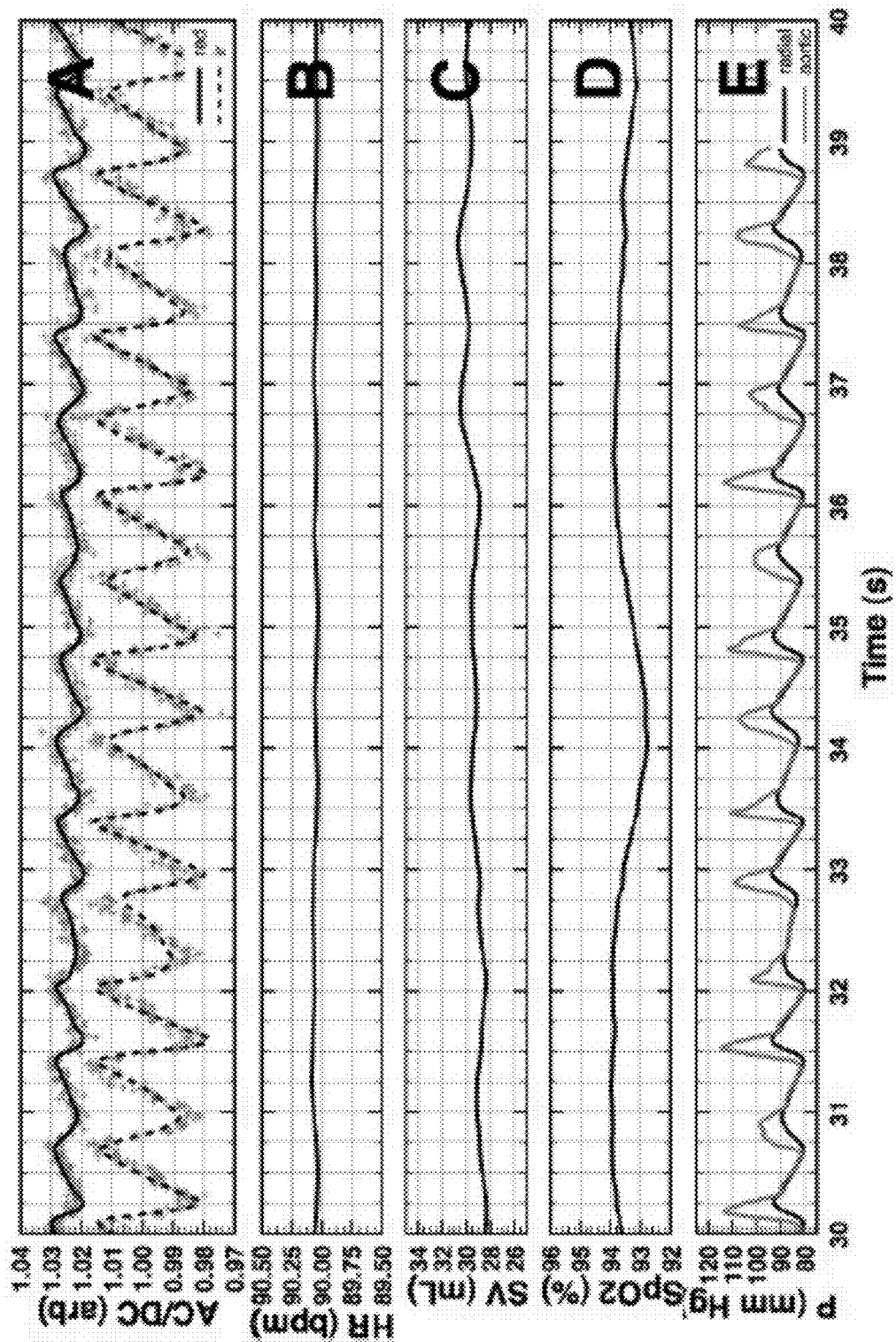
FIG. 12 is a chart showing input sensor data from a fingertip pulse oximeter and processed output data from a data processor configured to process pulse oximetry data under a low blood perfusion condition.

A calibration constant c was used to match the variance of the real lac/ldc signal with the variance of the DSSM-generated signal for each wavelength. After calibration, the age and gender of the patient was entered. Estimates for the means and covariances of both state and parameter PDFs were entered. FIG. 11 plots estimates for a 15 s stretch of data. Photoplethysmographic (PPG) waveforms (A) were used to extract heart rate (B), SV (C), CO (D), blood oxygen saturation (E), and aortic and systemic (radial) pressure waveforms (F). Results of processing pulse oximetry at low blood perfusion are shown in FIG. 12. Low signal-to-noise PPG waveforms (A) were used to extract heart rate (B), SV (C), blood oxygen saturation (D), and aortic and systemic (radial) pressure waveforms (E).

Electrocardiograph with Probabilistic Data Processing

Figure 10:
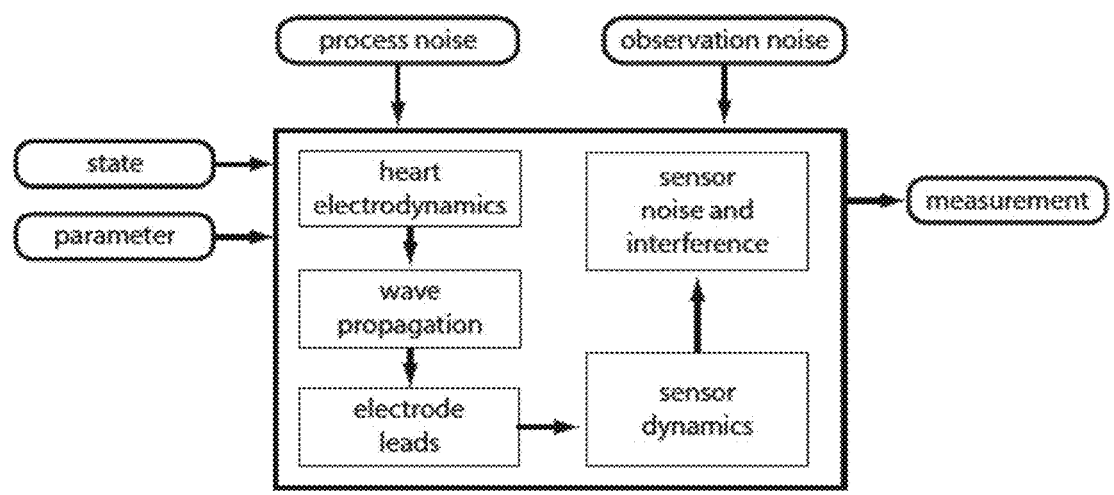
FIG. 10 is a flow chart showing the components of a DSSM used for electrocardiography data processing.

FIG. 10 is a schematic of a DSSM suitable for processing electrocardiograph data, including components required to describe the processes occurring in a subject. The combination of SPKF or SMC in state, joint or dual estimation modes can be used to filter electrocardiography (ECG) data. Any physiology model adequately describing the ECG signal can be used, as well as any model of noise and artifact sources interfering or contaminating the signal. One non-limiting example of such a model is the ECG signal generator proposed by McSharry (IEEE Transactions on Biomedical Engineering, 2003. 50(3):289-294). Briefly, this model uses a sum of Gaussians with amplitude, center and standard deviation, respectively, for each wave (P, Q, R, S, T-, T+15) in an ECG. The observation model comprises the state plus additive Gaussian noise, but more realistic pink noise or any other noise distributions can be used.

Figure 13:
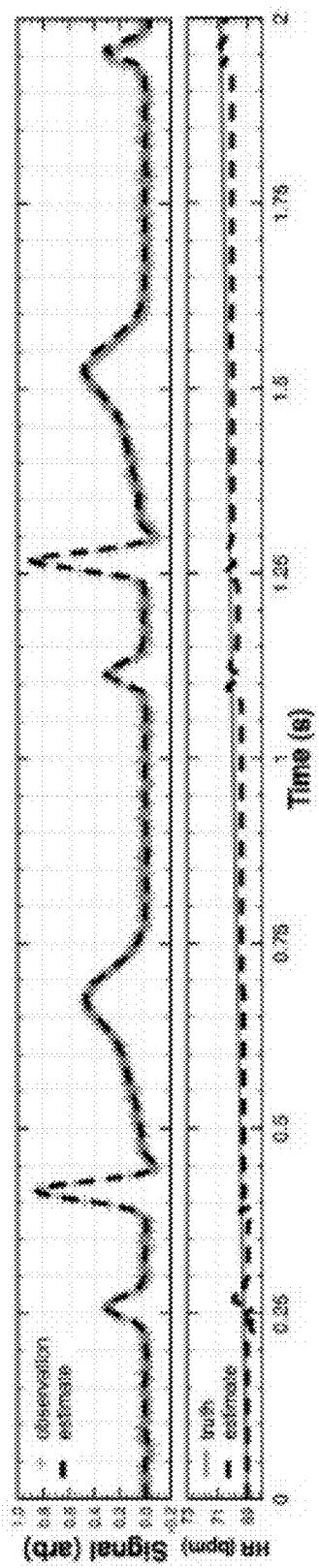
FIG. 13 is a chart showing noisy non-stationary ECG sensor data input and processed heart rate and ECG output for a data processor configured to process ECG sensor data.
Figure 14:
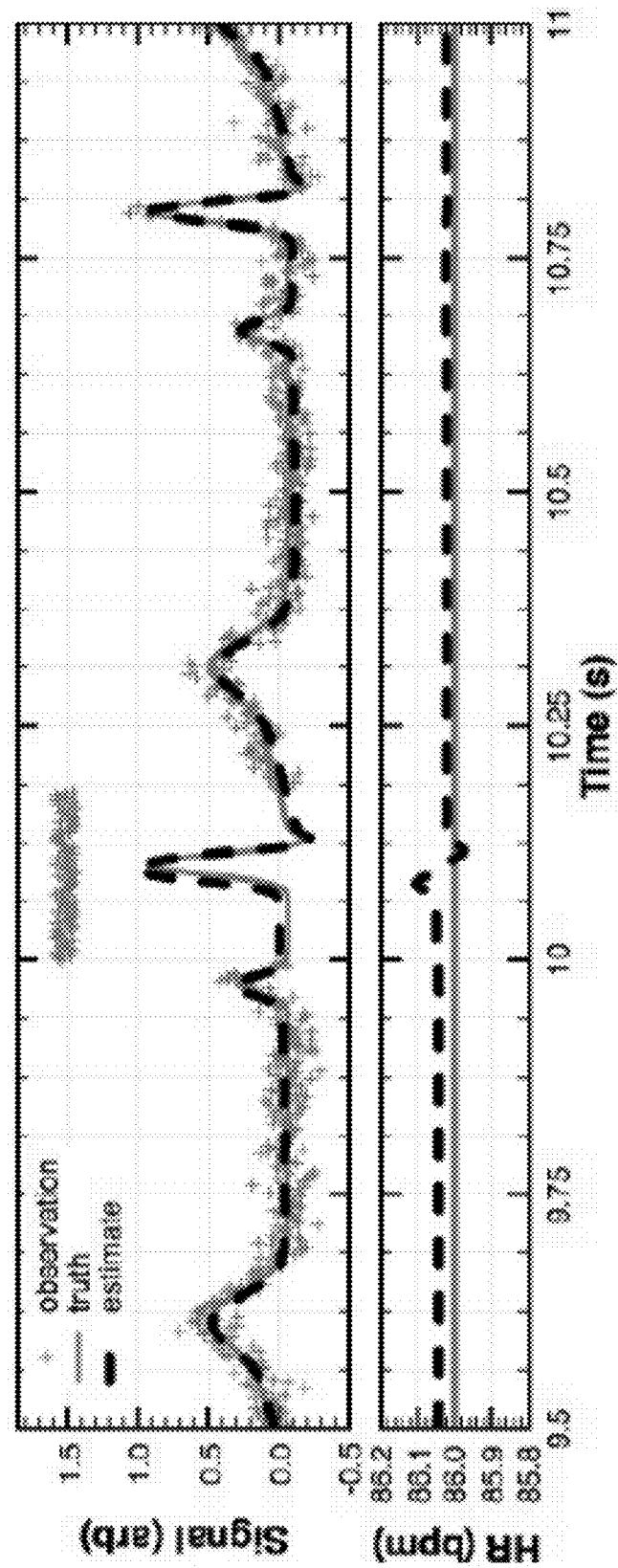
FIG. 14 is a chart showing input ECG sensor data and comparing output data from a data processor according to the present invention with output data generating using a Savitzky-Golay FIR data processing algorithm.

FIG. 13 shows the results of processing a noisy non-stationary ECG signal. Heart rate oscillations representative of normal respiratory sinus arrhythmia are present in the ECG. The processor accomplishes accurate, simultaneous estimation of the true ECG signal and heart rate that follows closely the true values. The performance of the processor in a noise and artifact-corrupted signal is shown in FIG. 14. A clean ECG signal representing one heart beat (truth) was contaminated with additive noise and an artifact in the form of a plateau at R and S peaks (beginning at time=10 s). Estimates by the processor remain close to the true signal despite the noise and artifact.

While a specific DSSMs and input and output parameters are provided for the purpose of describing the present method, the present invention is not limited to the DSSMs, sensors, biological monitoring devices, inputs, outputs, except as defined by the following claims.

The invention claimed is:

1. A system for non-invasively measuring left ventricular stroke volume (SV) and/or cardiac output (CO) of a patient, said system comprising:
   a pulse oximeter, a data processor, and means for generating an output reporting a measured SV or CO value to a user wherein:
   the pulse oximeter is configured to collect plethysmographic waveform data of the patient and to transmit the plethysmographic waveform data to the data processor;
   the data processor is configured to receive said plethysmographic waveform data and comprises software that calculates the measured value for SV and/or CO using said plethysmographic waveform data and reports the measured value for SV and/or CO to the user;
   the software that calculates a measured value for SV and/or CO from plethysmographic waveform data comprises a probabilistic processor and a mathematical model of a cardiovascular system integrated in a dynamic state space model (DSSM); and the mathematical model of the cardiovascular system comprises aortic pressure, radial pressure, peripheral resistance, aortic impedance, heart rate, stroke volume, and blood density as state or model parameters.

2. The system of claim 1, wherein the pulse oximeter is configured to collect plethysmographic waveform data of the patient and to transmit the plethysmographic waveform data to the data processor in real time.

3. The system of claim 1, wherein the software calculates the measured value for SV and/or CO in real time.

4. The system of claim 1, wherein the DSSM is integrated with a dual estimation processor engine or a joint estimation processor engine.

5. The system of claim 1, wherein the means for generating an output reporting measured SV or CO values to a user comprises means for generating an electronic display, a hard copy display, an audible sound, a visual display, or a tactile output.

6. The system of claim 1, wherein the pulse oximeter is a fingertip pulse oximeter.

7. The system of claim 1, wherein the mathematical model of a cardiovascular system includes model and/or state parameters that correspond directly to one or more of peripheral blood oxygen saturation ($SpO_2$), heart rate (HR), respiratory rate (RR), and blood pressure (BP).

8. The system of claim 7, wherein the data processor is additionally configured to receive data from a direct measurement of one or more of $SpO_2$, HR, RR, and BR.

9. The system of claim 1, further comprising a blood pressure measuring device that transmits blood pressure data to the processor and wherein the processor receives said blood pressure data to be used as input into the cardiovascular model.

10. The system of claim 1, wherein the processor comprises a processing engine within an executable program that is configured to receive digital data from the pulse oximeter and to output stroke volume data and/or cardiac output data to a display.

11. The system of claim 1, wherein:
the DSSM receives first probability distributions for state and model parameters to produce a first probability distribution function (PDF) representing a first state;
data for a time t1 from the pulse oximeter and the first PDF are combined using a Bayesian statistical process to generate a second PDF that represents a state at time t1;
expectation values for the second PDF are calculated and, using the expectation values, updated state parameters for time t1 are combined with pulse oximeter data for time t1 to update the model parameters for time t2 in the DSSM;
expectation values are also entered into the DSSM as the state, in the form of a vector of state parameters;
after the state parameters and model parameters for the DSSM are updated to time t1, the process is repeated with pulse oximeter data for time t2 to produce updated parameters for time t2;
and the processor is configured to process the parameters to generate an output related to ventricular stroke volume.

12. The system of claim 11, wherein the state parameters and model parameters are concatenated into a single vector that is transformed by the DSSM.

* * * * *